(12) United States Patent
Byerly

(10) Patent No.: US 10,857,304 B2
(45) Date of Patent: Dec. 8, 2020

(54) DETERMINATION OF A DOSE SET AND DELIVERED IN A MEDICATION DELIVERY DEVICE

(71) Applicant: Eli Lilly and Company, Indianapolis, IN (US)

(72) Inventor: Roy H. Byerly, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 162 days.

(21) Appl. No.: 16/082,481

(22) PCT Filed: Mar. 17, 2017

(86) PCT No.: PCT/US2017/022869
§ 371 (c)(1),
(2) Date: Sep. 5, 2018

(87) PCT Pub. No.: WO2017/165207
PCT Pub. Date: Sep. 28, 2017

(65) Prior Publication Data
US 2019/0091409 A1  Mar. 28, 2019

Related U.S. Application Data

(60) Provisional application No. 62/313,260, filed on Mar. 25, 2016.

(51) Int. Cl.
*A61M 5/315* (2006.01)

(52) U.S. Cl.
CPC ...... *A61M 5/31568* (2013.01); *A61M 5/3155* (2013.01); *A61M 5/3157* (2013.01);
(Continued)

(58) Field of Classification Search
CPC .......... A61M 5/31533; A61M 5/31545; A61M 5/3155; A61M 5/31553; A61M 5/31556; A61M 5/31565; A61M 5/31573
See application file for complete search history.

(56) References Cited

U.S. PATENT DOCUMENTS

| 685,091 A | 10/1901 | Becton |
|---|---|---|
| 1,625,035 A | 4/1927 | Lilly |

(Continued)

FOREIGN PATENT DOCUMENTS

| EP | 0338806 | 10/1989 |
|---|---|---|
| EP | 0498737 | 8/1992 |

(Continued)

OTHER PUBLICATIONS

Patent Cooperation Treaty International Search Report and Written Opinion of the International Searching Authority pertaining to International Application No. PCT/US2017/022869; dated Jul. 4, 2017.

(Continued)

*Primary Examiner* — Deanna K Hall
(74) *Attorney, Agent, or Firm* — Arthur C. H. Shum

(57) ABSTRACT

Sensing systems are disclosed for determining the relative rotational movements of members of a medication delivery device which are proportional to the amount of a dose set and delivered by the medication delivery device. The sensing system comprises a first sensor component secured to a first member and a second sensor component secured to a second member. During dose setting, the second member is coupled to a third member which rotates relative to the first member in proportion to the dose set. During dose delivery, the second member is coupled to a fourth member which rotates relative to the first member in proportion to the dose delivered. The sensing system separately detects the relative rotational positions of the first and second sensor components during dose setting and dose delivery, and provides outputs used to determine the amounts of the set and delivered doses. The sensing system outputs this information to a controller which determines the amount of the dose (Continued)

set and delivered. Related medication delivery devices and methods are also disclosed.

24 Claims, 4 Drawing Sheets

(52) U.S. Cl.
CPC .... *A61M 5/31533* (2013.01); *A61M 5/31545* (2013.01); *A61M 5/31553* (2013.01); *A61M 5/31556* (2013.01); *A61M 5/31565* (2013.01); *A61M 5/31573* (2013.01); *A61M 2205/18* (2013.01); *A61M 2205/3317* (2013.01); *A61M 2205/3327* (2013.01)

(56) References Cited

U.S. PATENT DOCUMENTS

| | | |
|---|---|---|
| 2,853,586 A | 9/1958 | Vercesi |
| 3,399,368 A | 8/1968 | Elliott et al. |
| 3,723,061 A | 3/1973 | Stahl |
| 4,315,252 A | 2/1982 | Tagami |
| 4,486,891 A | 12/1984 | Kimoto et al. |
| 4,529,401 A | 7/1985 | Leslie et al. |
| 4,552,055 A | 11/1985 | Foxwell |
| 4,592,745 A | 6/1986 | Rex et al. |
| 4,865,591 A | 9/1989 | Sams |
| 4,883,472 A | 11/1989 | Michel |
| 4,931,041 A | 6/1990 | Faeser |
| 5,279,586 A | 1/1994 | Balkwill |
| 5,418,362 A | 5/1995 | Lusby et al. |
| 5,509,905 A | 4/1996 | Michel |
| 5,536,249 A | 7/1996 | Castellano et al. |
| 5,569,212 A | 10/1996 | Brown |
| 5,582,598 A | 12/1996 | Chanoch |
| 5,593,390 A | 1/1997 | Castellano et al. |
| 5,626,566 A | 5/1997 | Petersen et al. |
| 5,628,309 A | 5/1997 | Brown |
| 5,674,204 A | 10/1997 | Chanoch |
| 5,688,251 A | 11/1997 | Chanoch |
| 5,691,646 A | 11/1997 | Sasaki |
| 5,704,922 A | 1/1998 | Brown |
| 5,728,074 A | 3/1998 | Castellano et al. |
| 5,743,889 A | 4/1998 | Sams |
| 5,820,602 A | 10/1998 | Kovelman et al. |
| 5,827,232 A | 10/1998 | Chanoch et al. |
| 5,920,198 A | 7/1999 | Suzuki et al. |
| 5,921,966 A | 7/1999 | Bendek et al. |
| 5,925,021 A | 7/1999 | Castellano et al. |
| 5,938,642 A | 8/1999 | Burroughs et al. |
| 5,954,700 A | 9/1999 | Kovelman |
| 5,957,896 A | 9/1999 | Bendek et al. |
| 5,961,496 A | 10/1999 | Nielsen et al. |
| 6,001,089 A | 12/1999 | Burroughs et al. |
| 6,004,297 A | 12/1999 | Steenfeldt-Jensen et al. |
| D425,990 S | 5/2000 | Gravel et al. |
| 6,068,615 A | 5/2000 | Brown et al. |
| 6,080,090 A | 6/2000 | Taylor et al. |
| 6,110,152 A | 8/2000 | Kovelman |
| 6,192,891 B1 | 2/2001 | Gravel et al. |
| 6,221,046 B1 | 4/2001 | Burroughs et al. |
| 6,221,053 B1 | 4/2001 | Walters et al. |
| 6,235,004 B1 | 5/2001 | Steenfeldt-Jensen et al. |
| 6,248,095 B1 | 6/2001 | Giambattista et al. |
| 6,277,099 B1 | 8/2001 | Strowe et al. |
| 6,302,855 B1 | 10/2001 | Lav et al. |
| 6,340,357 B1 | 1/2002 | Poulsen et al. |
| 6,482,185 B1 | 11/2002 | Hartmann |
| 6,540,672 B1 | 4/2003 | Simonsen et al. |
| 6,558,320 B1 | 5/2003 | Causey, III et al. |
| 6,585,698 B1 | 7/2003 | Packman et al. |
| 6,663,602 B2 | 12/2003 | Moller |
| 6,781,522 B2 | 8/2004 | Sleva et al. |
| 6,875,195 B2 | 4/2005 | Choi |
| 7,138,806 B2 | 11/2006 | Gafner et al. |
| 7,195,616 B2 | 3/2007 | Diller et al. |
| 7,704,238 B2 | 4/2010 | Diller et al. |
| 7,992,460 B2 | 8/2011 | Bochen et al. |
| 8,049,519 B2 | 11/2011 | Nielsen et al. |
| 8,197,449 B2 | 6/2012 | Nielsen et al. |
| 8,529,520 B2 | 9/2013 | Daniel |
| 8,556,865 B2 | 10/2013 | Krulevitch et al. |
| 8,672,899 B2 | 3/2014 | Diller et al. |
| 2001/0013774 A1 | 8/2001 | Noltemeyer et al. |
| 2002/0013522 A1 | 1/2002 | Lav et al. |
| 2002/0020654 A1 | 2/2002 | Eilersen |
| 2002/0120235 A1 | 8/2002 | Enggaard |
| 2002/0177923 A1 | 11/2002 | Steffen |
| 2003/0006209 A1 | 1/2003 | Stefen et al. |
| 2005/0182358 A1 | 8/2005 | Veit et al. |
| 2005/0182360 A1 | 8/2005 | Yeandel et al. |
| 2007/0123829 A1 | 5/2007 | Atterbury et al. |
| 2008/0140018 A1 | 6/2008 | Enggaard |
| 2009/0318865 A1 | 12/2009 | Møller et al. |
| 2010/0106098 A1 | 4/2010 | Atterbury et al. |
| 2012/0238960 A1 | 9/2012 | Smith et al. |
| 2013/0072897 A1 | 3/2013 | Day et al. |
| 2013/0310756 A1 | 11/2013 | Whalley et al. |
| 2014/0074041 A1 | 3/2014 | Pedersen et al. |
| 2014/0194829 A1 | 7/2014 | Baek et al. |
| 2014/0243750 A1 | 8/2014 | Larsen et al. |
| 2015/0018775 A1 | 1/2015 | Groeschke et al. |
| 2015/0174330 A1 | 6/2015 | Nagel et al. |
| 2015/0320934 A1 | 11/2015 | Draper et al. |
| 2015/0343152 A1 | 12/2015 | Butler et al. |
| 2016/0008552 A1 | 1/2016 | Madsen et al. |
| 2016/0015902 A1* | 1/2016 | Draper .................. A61M 5/20 604/207 |
| 2016/0136353 A1 | 5/2016 | Adams |
| 2016/0259913 A1 | 9/2016 | Yu et al. |
| 2016/0296702 A1 | 10/2016 | Rasmussen et al. |
| 2016/0378951 A1 | 12/2016 | Gofman et al. |
| 2017/0023204 A1 | 1/2017 | Takeuchi et al. |
| 2017/0128674 A1 | 5/2017 | Butler et al. |
| 2017/0189625 A1 | 7/2017 | Cirillo et al. |
| 2017/0274148 A1 | 9/2017 | Mews et al. |

FOREIGN PATENT DOCUMENTS

| | | |
|---|---|---|
| EP | 0519137 | 12/1992 |
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| EP | 1240913 | 9/2002 |
| EP | 2060284 | 5/2009 |
| EP | 2468340 | 6/2012 |
| EP | 2692378 | 2/2014 |
| GB | 2309801 | 8/1997 |
| WO | 9009202 | 8/1990 |
| WO | 9619872 | 6/1996 |
| WO | 0041754 | 7/2000 |
| WO | 0077472 | 12/2000 |
| WO | 0110484 | 2/2001 |
| WO | 0156635 | 8/2001 |
| WO | 0159570 | 8/2001 |
| WO | 02064196 | 8/2002 |
| WO | 02092153 | 11/2002 |
| WO | 03009461 | 1/2003 |
| WO | 03015838 | 2/2003 |
| WO | 03005891 | 11/2003 |
| WO | 2006045525 | 5/2006 |
| WO | 2011064299 | 6/2011 |
| WO | 2012004298 | 1/2012 |
| WO | 2013010893 | 1/2013 |
| WO | 2013098421 | 7/2013 |
| WO | 2014037331 | 3/2014 |
| WO | 2014128157 | 8/2014 |
| WO | 2015002806 | 1/2015 |
| WO | 2015123688 | 8/2015 |

(56) References Cited

FOREIGN PATENT DOCUMENTS

| WO | 2016180873 | 11/2016 |
| WO | 2017021226 | 2/2017 |
| WO | 2017092960 | 6/2017 |
| WO | 2017165207 | 9/2017 |
| WO | 2018031390 | 2/2018 |
| WO | 2018111708 | 6/2018 |
| WO | 2018111709 | 6/2018 |

OTHER PUBLICATIONS

Eli Lilly and Company, Technical Dossier for the HumaPen® Pen-Injector Family, Aug. 15, 2000, pp. 1 and 10-25 provided.
Soft Pot potentiometers https://media.digikey.com/pdf/Data%20Sheets/Spectra%20Symbol/SP%20Series%20SoftPot.pdf.
Hoffman-Krippner potentiometers http://www.hoffmann-krippner.com/potentiometers-sensofoil.pdf.
State Electronics potentiometers http://www.potentiometers.com.

\* cited by examiner

DETERMINATION OF A DOSE SET AND DELIVERED IN A MEDICATION DELIVERY DEVICE

CROSS-REFERENCE TO RELATED APPLICATIONS

This application is the National Stage of International Application No. PCT/US2017/022869, filed Mar. 17, 2017, which claims priority to U.S. provisional patent application Ser. No. 62/313,260 filed on Mar. 25, 2016, which is hereby incorporated herein by reference.

BACKGROUND

The present invention pertains to medication delivery devices, and in particular to a sensing system in a medication delivery device.

A variety of medication delivery devices, including for example pen injectors, infusion pumps and syringes, are commonly used for periodic delivery of medications. It is important that the proper amount of medication be supplied at these times as the health of the patient is at stake. In many instances, failure to accurately deliver the appropriate amount of medication may have serious implications for the patient.

The delivery of a proper amount of medication requires that the actual dosing by the medication delivery device be accurate. The term "dosing" as used herein refers to the two key phases of delivering a dose, namely, setting the dose amount and delivering the amount of the set dose. Assuring that an accurate dose is delivered requires that the medication delivery device performs properly during both of these key phases of dosing.

Medication delivery devices generally utilize mechanical systems in which various members rotate or translate relative to one another. In most instances, these relative movements between members are proportional to the dose amount set and/or delivered by operation of the device. Accordingly, the art has endeavored to provide reliable systems that accurately measure the relative movement of members of a medication delivery device in order to assess the dose set and/or delivered. Such systems may include a sensor which is secured with a first member of the medication delivery device and detects the relative movement of a sensed component secured to a second member of the device. The prior art has described a variety of sensing systems based upon the movement of objects through a sensed area, including optical, tactile, electrical and magnetic systems.

SUMMARY

In one form thereof, the present invention provides a sensing system for determining both the amount of a dose set and the amount of a dose delivered by operation of a medication delivery device, the sensing system comprising a first member of the medication delivery device; a second member of the medication delivery device, the second member being rotatable relative to the first member; a third member of the medication delivery device rotatable relative to the first member during dose setting in proportion to the amount of a dose set by operation of the medication delivery device; a fourth member of the medication delivery device rotatable relative to the first member during dose delivery in proportion to the amount of a dose delivered by operation of the medication delivery device; the second member being rotationally coupled with the third member and not the fourth member during dose setting to rotate with the third member during dose setting, the second member being rotationally coupled with the fourth member and not the third member during dose delivery to rotate with the fourth member during dose delivery; a first sensor component secured with the first member; and a second sensor component secured with the second member, one of the first and second sensor components being a sensor and the other of the sensor components being a target, the sensor being operable during dose setting to detect the rotation of the target relative to the sensor and to generate at least one first output correlated thereto, and the sensor being operable during dose delivery to detect the rotation of the target relative to the sensor and to generate at least one second output correlated thereto.

In another form thereof, the present invention provides a medication delivery device for determining both the amount of a dose set and the amount of a dose delivered by operation of the medication delivery device, comprising: a first member; a second member rotatable relative to the first member; a third member rotatable relative to the first member during dose setting in proportion to the amount of a dose set by operation of the medication delivery device; a fourth member rotatable relative to the first member during dose delivery in proportion to the amount of a dose delivered by operation of the medication delivery device; the second member being rotationally coupled with the third member and not the fourth member during dose setting to rotate with the third member during dose setting, the second member being rotationally coupled with the fourth member and not the third member during dose delivery to rotate with the fourth member during dose delivery; a first sensor component secured with the first member; and a second sensor component secured with the second member, one of the first and second sensor components being a sensor and the other of the sensor components being a target, the sensor being operable during dose setting to detect the rotation of the target relative to the sensor and to generate at least one first output correlated thereto, and the sensor being operable during dose delivery to detect the rotation of the target relative to the sensor and to generate at least one second output correlated thereto.

The present invention provides a sensing system for detecting relative rotational movement of members in a medication delivery device. The sensing system is used in conjunction with members of a medication delivery device that move relative to one another during dose setting and during dose delivery in a manner that is proportional to the amount of the set and the delivered dose. The sensing system includes a first sensor component secured to a first member, and a second sensor component secured to a second member rotatable relative to the first member. The second member is coupled during dose setting with a third member which rotates relative to the first member in proportion to the amount of dose set. The second member is coupled during dose delivery with a fourth member which rotates relative to the first member in proportion to the amount of dose delivered. The set and delivered doses are determined based on the detected relative rotational movements.

One advantage of the present invention is that a sensing system may be provided that provides an accurate and reliable assessment of the amount of medication that has been set and delivered by a medication delivery device.

Another advantage of the present invention is that a sensing system may be provided that requires few individual parts, and is compact and readily adapted to a variety of medication delivery devices.

Further objects, features and embodiments of the present invention will become apparent from the detailed description and drawings provided herewith.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
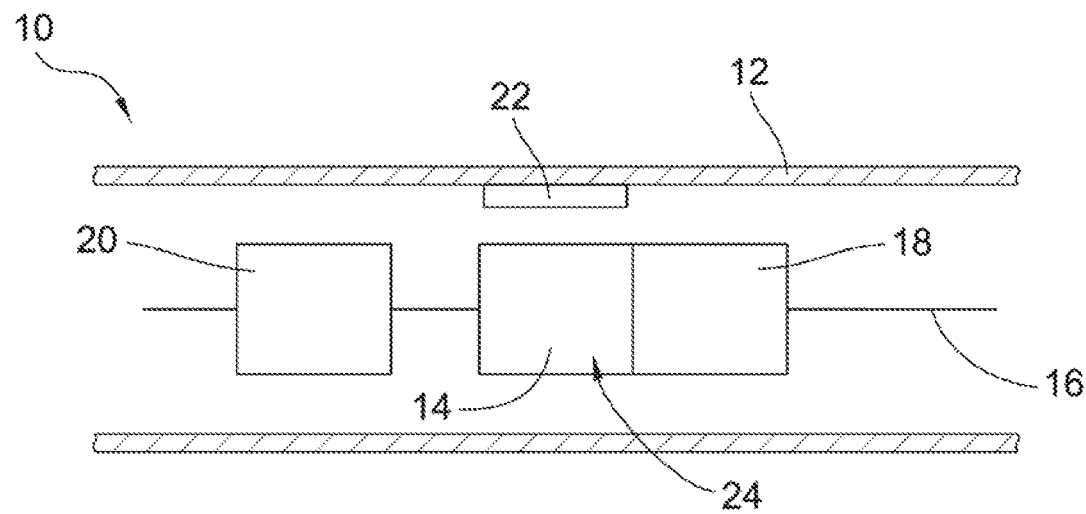
FIG. 1 is a schematic diagram of a sensing system in a first position during dose setting.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

For the purpose of promoting an understanding of the principles of the invention, references are made herein to examples illustrated in the drawings, and specific language is used to describe the same. It will nevertheless be understood that no limitation of the scope of the invention is thereby intended. Any alterations and further modifications in the described embodiments, and any further applications of the concepts disclosed herein, are contemplated as would normally occur to one skilled in the relevant art. Examples of these concepts are shown in detail, but it will be apparent that some features and details have been omitted for the sake of clarity.

The present invention relates generally to sensing systems for determining both the amount of a dose set and the amount of a dose delivered by a medication delivery device. The amounts are determined based on the measurement of relative rotational movement between members of the medication delivery device, where the measured movements are correlated to the amount of the dose set and the dose delivered. The medication delivery device may be any device which is used to set and to deliver a dose of a medication, such as pen injectors, infusion pumps and syringes. The medication may be any of a type that may be delivered by such a medication delivery device.

The sensing system includes a first sensor component secured with a first member of the medication delivery device, and a second sensor component secured with a second member of the medication delivery device. The second member is free to rotate relative to the first member during both dose setting and dose delivery.

During dose setting, the second member is coupled with a third member which rotates relative to the first member in an amount proportional to the amount of dose set by the medication delivery device. The rotation of the second sensor component relative to the first sensor component during dose setting therefore correlates to the relative rotation of the first and third members, which is proportional to the amount of dose set. This relative rotation is used to determine the amount of the dose set.

During dose delivery, the second member is coupled with a fourth member which rotates relative to the first member in an amount proportional to the amount of dose delivered by the medication delivery device. The rotation of the second sensor component relative to the first sensor component during dose delivery therefore correlates to the relative rotation of the first and fourth members, which is proportional to the amount of dose delivered. This relative rotation is used to determine the amount of the dose delivered.

Figure 2:
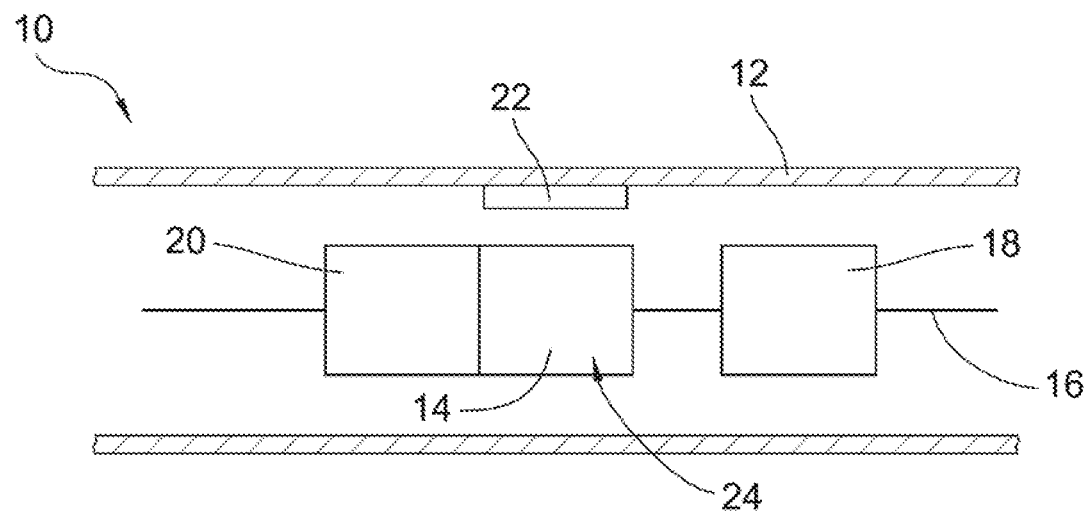
FIG. 2 is a schematic diagram of the sensing system of FIG. 1 in a second position during dose delivery.

Referring to FIGS. 1 and 2, there is shown a sensing system 10 comprising a first member 12, and a second member 14 which is rotatable relative to the first member 12 about axis 16. A third member 18 rotates relative to first member 12 about axis 16 in proportion to the amount of dose set. A fourth member 20 rotates relative to first member 12 about axis 16 in proportion to the amount of dose delivered. Secured to the first member 12 is a first sensor component 22. Secured to the second member 14 is a second sensor component 24, positioned to be sensed by first sensor component 22 during relative rotation between the first member 12 and the second member 14.

Shown schematically in FIG. 1 is the sensing system as it operates during dose setting. Second member 14 is coupled with third member 18 to rotate with the third member during dose setting. In this manner, the rotation of second member 14 is proportional to the amount of dose set, and this rotation relative to first member 12 may be detected by operation of the sensor components 22 and 24. The fourth member 20 is typically fixed against rotation relative to the first member during dose setting.

As shown in FIG. 2, the sensing system 10 during dose delivery has the second member 14 instead coupled with fourth member 20 to rotate with the fourth member. Second member 14 therefore rotates during dose delivery in proportion to the amount of the dose delivered, and this rotation may be detected by the sensor components. Third member 18 is typically fixed against rotation relative to the first member during dose delivery.

The sensing system uses sensor components that are secured with members of the medication delivery device. As used herein, the term "secured" encompasses any manner of fixing, to the extent required for system operation, the position of a sensor component to the associated member of the medication delivery device. For example, a sensor component may be directly positioned on, received within, attached to, or integral with the associated member. Alternatively, there may be one or more other components which indirectly connect the sensor component with the member. It will be appreciated by those skilled in the art that the sensor components are sufficiently "secured" to the respective members if they are thereby caused to move in unison with or in proportion to the members of the medication delivery device as those members move relative to one another during dose setting and delivery.

The sensing system operates with the second member alternately being coupled with either the third member or the fourth member. As used herein, the term "coupled" encompasses any manner by which one member is secured to rotate in unison with or in proportion to another member as the other member rotates. Coupling systems may include, for example, connections provided through splines, gears or frictional engagement between the members, or similar connections provided by other components which indirectly couple the members.

The sensing system comprises first and second sensor components. One sensor component is a sensor, and the other is referred to herein as a target. The term "sensor" refers to any component which is able to detect the relative rotational position of the target. A "target" is any component which moves relative to the sensor and for which the sensor is able to detect the rotational position of the target relative to the sensor. Thus, the sensor is able to monitor the position of the target and to provide outputs representative of the relative rotational movement of the target.

A sensor typically detects a characteristic of a sensed parameter which varies in relationship to the position of the target within a sensed area. The target extends into or otherwise influences the sensed area in a manner that directly or indirectly affects the sensed parameter. Each different position of the target presents a unique influence on the sensed area, which has an associated effect on the sensed parameter of the sensor. The different positions of the target therefore result in values for the sensed parameters that are characteristic of the relative positions of the sensor and the target.

The present invention is useful with any of a variety of sensing technologies that are known which operate based on any principle by which the movement of two relatively rotating members can be detected. Such technologies may include, for example, technologies based on tactile, optical or electrical measurements, including but not limited to grey scale measurements, indicating the position of one component relative to another. Such technologies may also include the measurement of a sensed parameter associated with a field, such as a magnetic or electric field, which is imposed upon the sensed area and which is altered based upon the position of the target within the field. The alterations of the field change the sensed parameter in direct relation to the position of the target in the sensed area. In such an embodiment, for example, the sensed parameter may be a capacitance, conductance, resistance, impedance or voltage. A suitable sensing technology uses a magnetic sensor. For example, in a magneto-resistive type sensor the distortion of an applied magnetic field results in a characteristic change in the resistance of an element of the sensor component. Similarly, Hall Effect sensors detect changes in voltage resulting from distortions in an applied magnetic field.

An advantageous sensing system is one which is a non-contact system, which therefore does not have the potential for components being susceptible to degradation due to wear resulting from repeated contact between the components. Further, suitable systems may include the combination of an active component and a passive component, with the sensor operating as the active component. In that manner, it is not necessary to have both components connected with other system elements such as a power supply or controller.

The sensor components detect relative rotational movement and produce associated outputs from which the movement may be determined. In general, the sensor may be operable during dose setting to detect the rotational positions of the target relative to the sensor and to generate at least one first output correlated thereto. The sensor may also be operable during dose delivery to detect the rotational positions of the target relative to the sensor and to generate at least one second output correlated thereto. A controller is operably connected to the sensor to receive the at least one first output and the at least one second output from the sensor. The controller is configured to determine from the outputs the amount of dose set and the amount of dose delivered by operation of the medication delivery device. In one embodiment, the sensor provides outputs relating to the relative start and stop positions of the rotating members during dose setting and during dose delivery. Alternatively, the sensor may provide a single output indicative of the overall rotation of the sensor relative to the target during dose setting and/or dose delivery.

For purposes of further illustration, the configuration and operation of the present invention is described in relation to a medication delivery device in the form of a pen injector, such as a pen injector used for the delivery of insulin for the treatment of diabetes. During dose setting and during dose delivery it is common that various members of the device rotate relative to one another. These members may vary depending on design of the medication delivery device, and may include, for example, a housing, dose knob, dial sleeve, drive sleeve, dosing nut and/or piston rod. It will be appreciated, however, that no limitation of the scope of the invention is intended by use of the following example. The invention is useful in connection with a wide variety of medication delivery devices in which the relative rotational movements of component members are indicative of both the amount of dose that is set and of the amount of dose that is delivered.

By way of example, sensing system 40 may include housing 42 in which is received a barrel 44 which is rotatable relative to the housing about axis 46. Barrel 44 is biased in the proximal direction (to the right in FIG. 3) by a spring 48 and clicker 50. Barrel 44 includes a flange 52 which rests against a shoulder 54 of housing 42 when the barrel is in the proximal position. In this position, circumferentially-spaced teeth 56 on barrel 44 are received and move freely within circumferential groove 58 of housing 42 during relative rotation of the barrel and the housing.

Barrel 44 has an alternate position moved distally such that barrel teeth 56 are received by complementary positioned teeth 60 of housing 42, locking the barrel against rotation relative to the housing. Alternately, the barrel may be locked by teeth on the barrel bottoming out within the teeth of clicker 50, which is keyed to housing 42.

Dial sleeve 62 is received within barrel 44. A key 64 on dial sleeve 62 is received within longitudinal keyway 66 in barrel 44. This allows the dial sleeve to move axially relative to the barrel, but prevents relative rotation between the two members. The dial sleeve includes tabs 68 and 70 which are engaged within external threads 72 of a drive sleeve 74. Rotation of dial sleeve 62 relative to drive sleeve 74 causes the dial sleeve to move axially as tabs 68 and 70 travel along threads 72.

Rotation of the drive sleeve is used to move a drive member to deliver a set dose. In one embodiment, for example, drive sleeve 74 is coupled with a drive nut (not shown) that has an internal thread, and which is axially fixed within the housing 42. The internal thread of the drive nut engages the external thread on the drive member, as hereafter described. In this embodiment, the rotation of the drive sleeve rotates the drive nut, which in turn advances the drive member distally to administer the set dose. It will be appreciated that various other ways are also well known in the art to use the rotational movement of the drive sleeve 74 to advance a drive member.

The setting of a dose for the foregoing device occurs as follows. Barrel 44 is initially in the proximal position relative to the housing 42 (FIG. 3) and rotates with the teeth 56 spinning freely within circumferential groove 58. Drive sleeve 74 is rotationally fixed by complementary splines (not shown) relative to housing 42. During dose setting, dial sleeve 62 is rotated and spirals up drive sleeve 74. The keyed connection of the barrel and the dial sleeve causes barrel 44 to rotate in unison with dial sleeve 62. However, barrel 44 at the same time is prevented from moving proximally relative to the housing in view of flange 52 being received against shoulder 54. There is therefore relative rotational movement between the barrel and the housing during dose setting which represents the amount of dose set by the medication delivery device. This rotational movement is detected by sensing system 40.

In order to deliver the set dose, dial sleeve 62 is manually pushed distally. The frictional engagement of the dial sleeve tabs 68 and 70 with the drive sleeve threads 72 is initially sufficient to prevent relative rotation and causes the drive sleeve 74 to advance with the dial sleeve without rotating relative to the housing. An outwardly-extending flange 76 of drive sleeve 74 rests adjacent an interior shoulder 78 of barrel 44 and therefore barrel 44 also moves distally. This movement causes the barrel teeth 56 to engage with the housing teeth 60. As a result, further distal movement of drive sleeve 74 and barrel 44 relative to housing 42 is prevented. Further, barrel 44 and keyed dial sleeve 62 are thus also locked against rotation relative to housing 42. However, dial sleeve 62 is free to move distally with respect to barrel 44 as the key 64 travels along keyway 66. This initial distal movement of drive sleeve 62 also disengages the splines fixing drive sleeve 74 from rotation relative to housing 42 during dose setting, and the drive sleeve is therefore free to rotate relative to the housing.

At this point, the dial sleeve 62 is free to move distally, but not rotationally, relative to housing 42, and drive sleeve 74 is free to rotate, but not move distally, relative to housing 44. Further force on dial sleeve 62 therefore overcomes the frictional engagement between the tabs 68 and 70 and drive sleeve threads 72, and drive sleeve 74 rotates relative to housing 42 as the dial sleeve advances non-rotationally. This rotation of the drive sleeve results in rotation of the drive nut and advancement of the drive member to deliver the dose as previously described. Thus, during dose delivery drive sleeve 74 rotates relative to housing 42 in an amount representative of the amount of dose delivered by the medication delivery device.

It may occur that a medication delivery device includes members which rotate relative to one another in proportion to the amount of dose delivered, but which also rotate at times when a dose is not delivered. In such a situation, the sensing system may be configured to account for this by measuring only that portion of the relative rotation that is correlated to the amount of dose set or delivered, or by measuring the full amount of rotation and reducing it by a known amount of rotation that is not correlated to dosing. This situation also may be accommodated, for example, by mathematical or other methods of compensation programmed into the controller. In any event, the principle remains the same that the sensing system determines the amount of dose setting or delivery in relation to that relative rotational movement of members that is indicative of the dosing.

The sensing system 40 further includes a sensor 80 secured with housing 42. A target 82 is secured to clutch 84 which is rotatable relative to housing 42 about axis 46. Clutch 84 may be fixed axially relative to housing 42 by way of a circumferential flange 86 received within a groove 88 in the interior wall of housing 42. This maintains target 82 in the proper position directly across from sensor 80 during all operations of the medication delivery device. It will be appreciated that these features may be reversed with the flange extending outwardly from the housing and the groove being formed in the outer wall of the clutch 84.

Alternatively, clutch 84 need not be fixed axially with housing 42, provided that sensor 80 is still operable to sense target 82 during both dose setting and dose delivery. In yet another embodiment, sensor 80 may be moveable axially relative to housing 42, and/or target 82 may be moveable axially relative to clutch 84, provided again that sensor 80 remains operable to sense target 82 during both dose setting and dose delivery.

Figure 3:
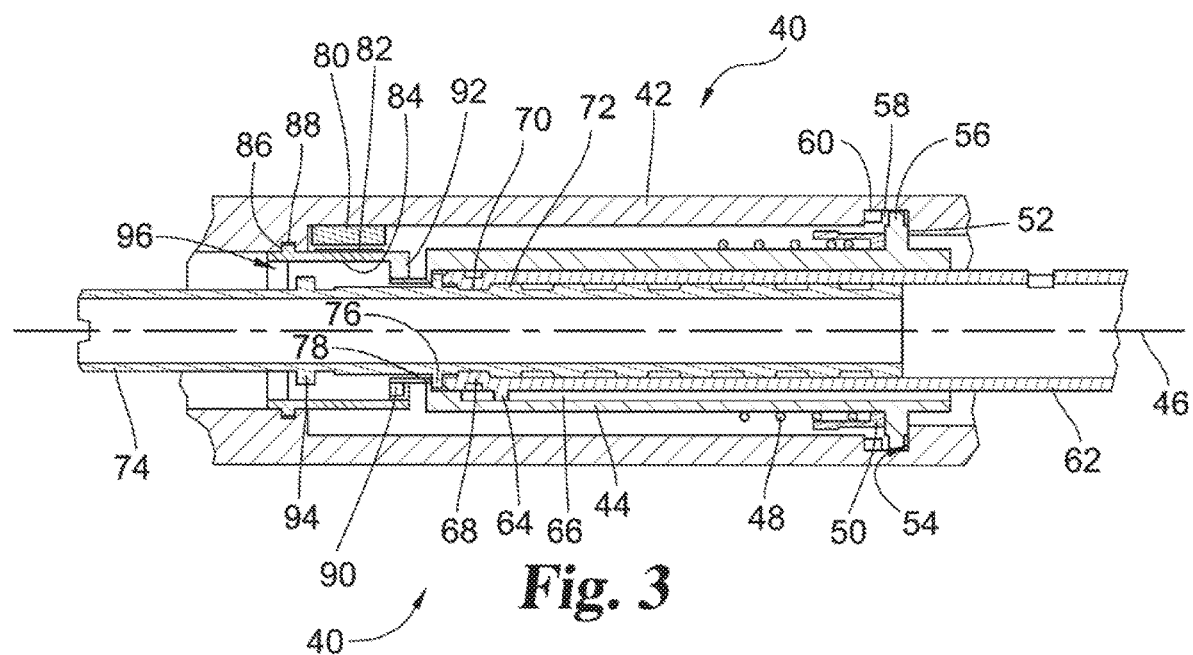
FIG. 3 is a partial, cross-sectional view of a sensing system in a setting position.
Figure 4:
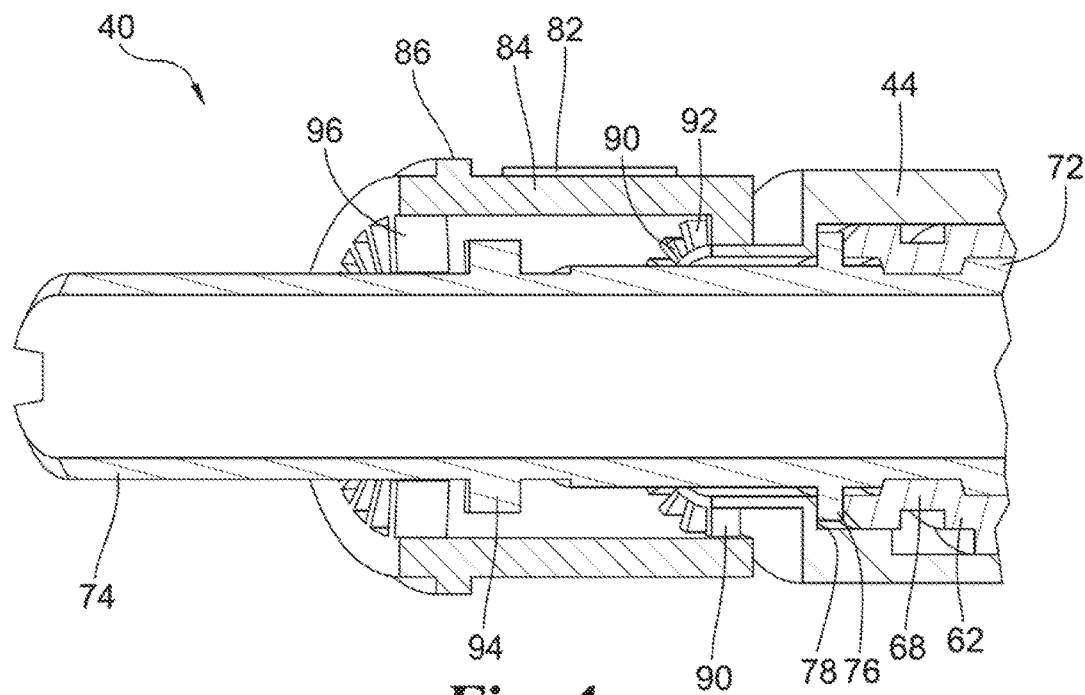
FIG. 4 is an enlarged, perspective view of a portion of the sensing system of FIG. 3.

The sensing system 40 is shown in FIGS. 3 and 4 with barrel 44 and drive sleeve 74 in a first position during which a dose may be set. In this position, barrel 44 includes splines 90 which are engaged with splines 92 of clutch 84. Dose setting is accomplished by rotating dial sleeve 62 relative to drive sleeve 74, and therefore also relative to housing 42. Barrel 44 is keyed to and rotates in unison with the dial sleeve relative to housing 42. Clutch 84 and target 82 are coupled with barrel 44 and therefore also rotate relative to housing 42 during dose setting. The rotation of clutch 84 relative to housing 42 during dose setting is directly proportional to the amount of dose set by the medication delivery device. The corresponding rotational movement of target 82 relative to sensor 80 is detected as an indication of the amount of dose set.

Figure 5:
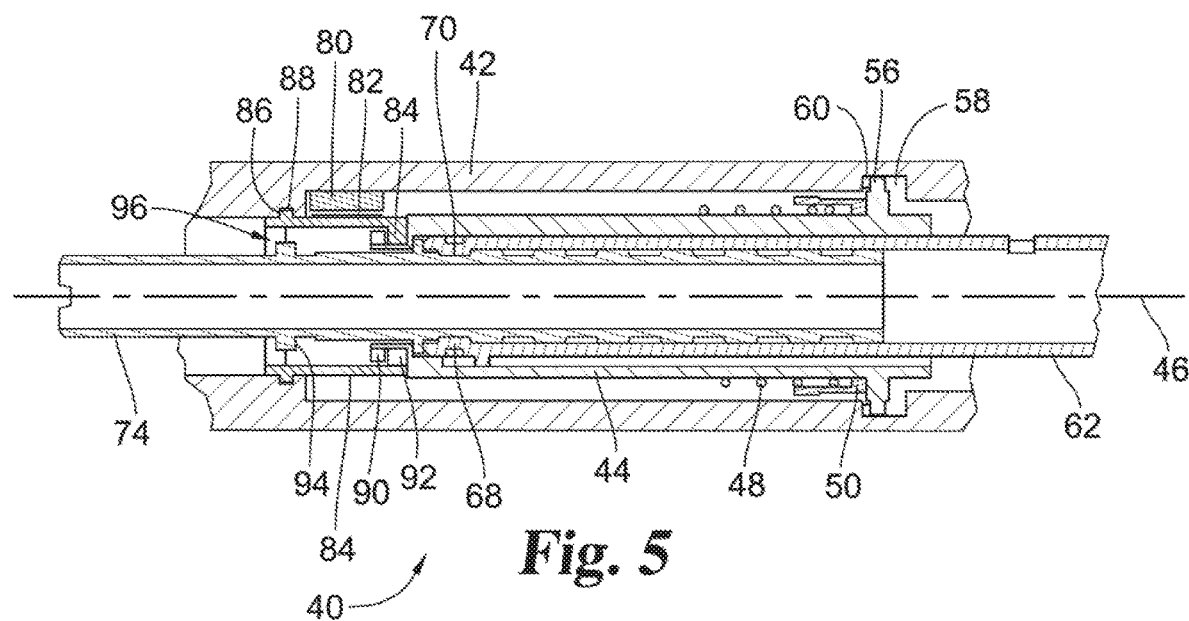
FIG. 5 is a partial, cross-sectional view of the sensing system of FIG. 3 in the delivery position.
Figure 6:
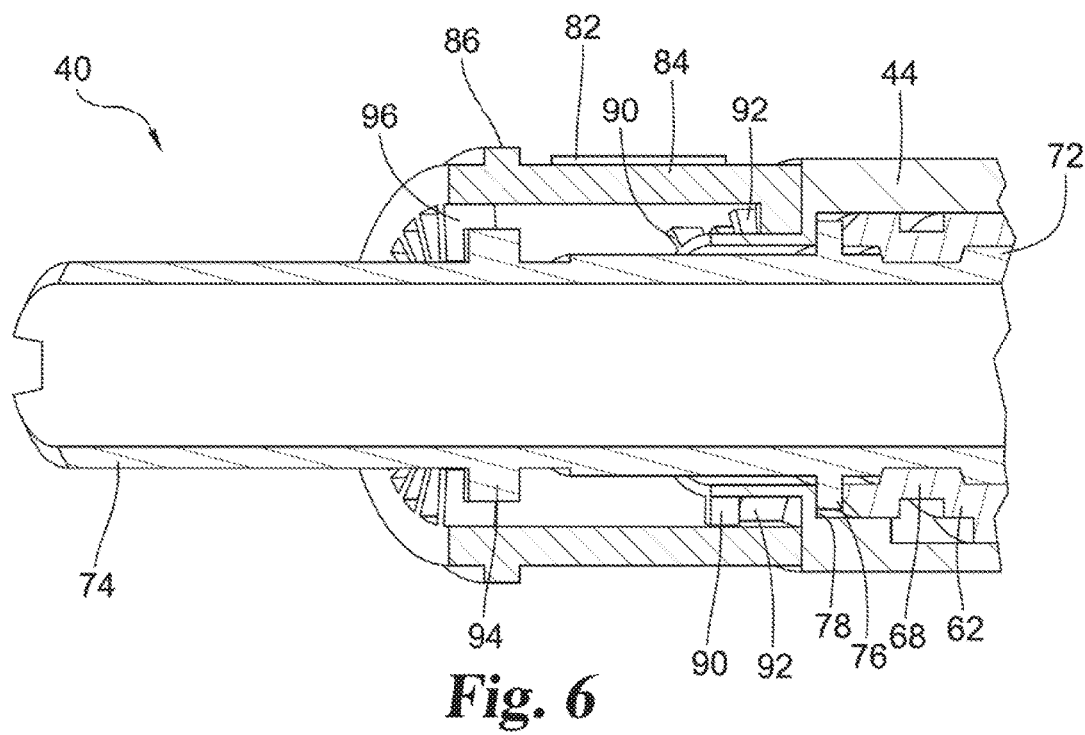
FIG. 6 is an enlarged, perspective view of a portion of the sensing system of FIG. 5.

Referring to FIGS. 5 and 6, clutch 84 is shown in a second position during which a dose may be delivered. This condition is obtained following a transition during which dial sleeve 62 is advanced the short distance required to engage the barrel teeth 56 with the housing teeth 60, locking the barrel from rotation relative to housing 42. With that same movement, the splined connection of drive sleeve 74 with housing 42 is released and the drive sleeve is free to rotate relative to housing 42.

This transitional movement also repositions barrel 44 and drive sleeve 74 relative to clutch 84. As shown for example in FIG. 6, the barrel splines 90 have moved distally a distance that disengages them from clutch splines 92. Clutch 84 is therefore free to rotate independently of the barrel. At the same time, splines 94 on drive sleeve 74 have moved distally and now engage with second splines 96 on clutch 84 to couple the drive sleeve and clutch rotationally. Relative rotation between the drive sleeve and the housing will therefore result in a corresponding relative rotation between target 82 and sensor 80. The rotation of clutch 84 relative to housing 42 during dose delivery is directly proportional to the amount of dose delivered by the medication delivery device. The corresponding rotational movement of target 82 relative to sensor 80 is detected as an indication of the amount of dose delivered.

The target is thus alternately coupled with one member during dose setting and a different member during dose delivery. In the described embodiment, this occurs by the clutch being coupled with the barrel during dose setting and with the drive sleeve during dose delivery. It will be appreciated, however, that the sensing system may instead be configured to have the clutch be coupled with whatever members provide the required relative rotation corresponding to dose setting and dose delivery, respectively.

Shown is an embodiment in which the coupling is accomplished by mutually-facing splines carried by the respective members. As mentioned previously, however, the members may be coupled in any other manner which causes the members to rotate together. For example, the coupling may comprise a variety of mechanical systems, including gears, splines, frictional couplings, or the like. It is well known in other arts, for example, that fluid shear couplings and other frictional couplings are useful to couple two members intended to rotate together. Further, the coupling need not directly rotatably connect one member to the other, but instead a completely separate component may indirectly couple the members together for rotation.

In a shown aspect, the coupling is effectuated as a result of the relative axial movement of the members. In the foregoing embodiment, for example, axial movement of barrel 44 in the proximal direction causes the barrel splines 90 to seat within first clutch splines 92 to couple the barrel rotationally with clutch 84. At the same time, the corresponding proximal movement of drive sleeve 74 causes drive sleeve splines 94 to withdraw from second clutch splines 96 to disconnect the drive sleeve from rotational coupling with clutch 84. Axial movement in the distal direction as a preliminary to dose delivery has the opposite effect. Thus, the coupling system operable during dose setting acts to couple the clutch and the barrel as a result of the axial movement of the barrel relative to the clutch. Similarly, the coupling system operable during dose delivery acts to couple the clutch with the drive sleeve upon axial movement of the drive sleeve relative to the clutch. In one embodiment the barrel and drive sleeve move axially in unison between the setting position and the delivery position to produce coupling and decoupling with the clutch.

Figure 7:
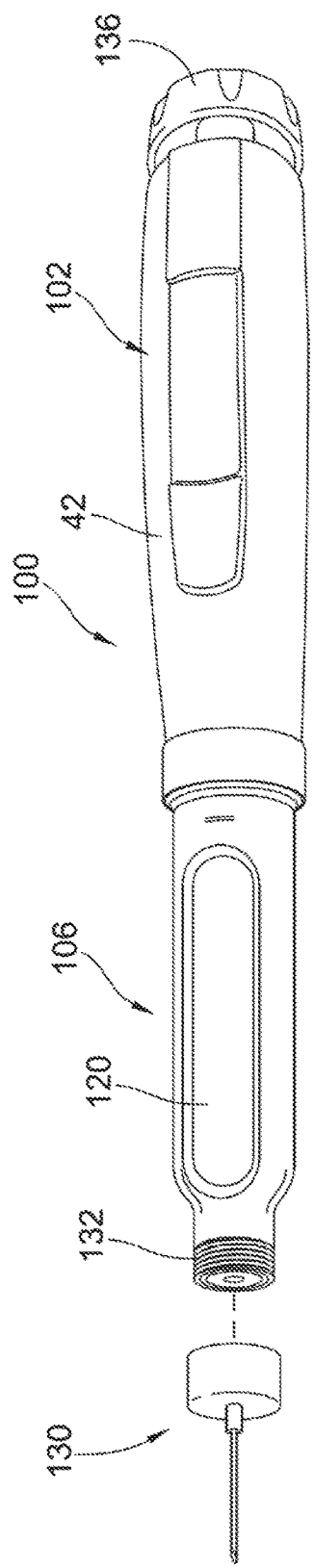
FIG. 7 is a plan view of a medication delivery device incorporating the sensing system of FIG. 3.
Figure 8:
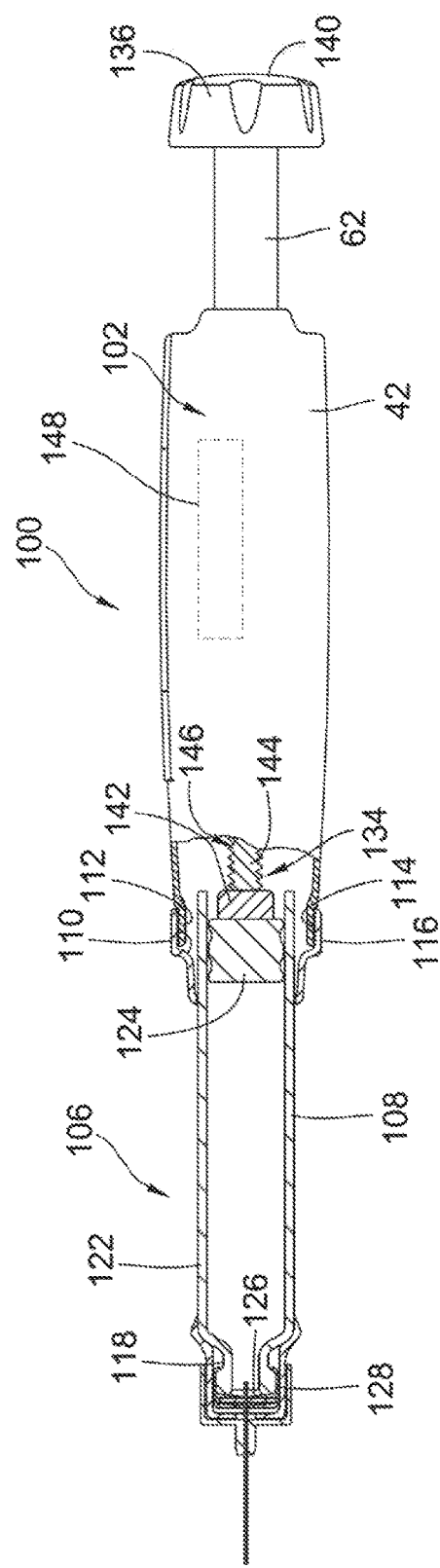
FIG. 8 is a plan view of the medication delivery device of FIG. 7 in partial cross section.

Referring now to FIGS. 7-8, there is shown an example of a medication delivery device incorporating the sensing system. The device comprises a pen-shaped delivery device 100 which is manually handled by a user to selectively set a dose and then to deliver that set dose. Delivery devices of this general type are well known, and the description herein of device 100 is merely illustrative. The sensing system is shown in use with this described embodiment, but it is readily adaptable for use in variously constructed medication delivery devices for which the relative movements of component members are indicative of the amount of a dose that is set and delivered.

Medication delivery device 100 includes a casing 102 that supports the internal components of the device. The casing is shown as having a housing 42 and a cartridge retainer 106. Housing 42 holds the mechanical drive mechanism, such as previously described with respect to FIGS. 3-6, which is operated to set and deliver a dose of medication. Cartridge retainer 106 holds a cartridge 108 filled with medication to be delivered by the device. Cartridge retainer 106 is detachably mountable to housing 42 via external threading 110 on a protruding collar portion 112 of housing 42 which mates with internal threading 114 on a ring portion 116 at the proximal end of cartridge retainer 106. Suitable detachable mounting elements other than threadings 110 and 114, such as a bayonet fitting, are known in the art and naturally may instead be employed.

Cartridge retainer 106 includes an internal hollow 118 suited to removably receive cartridge 108, thereby allowing a cartridge to be inserted therein, and then removed therefrom when depleted and replaced with a fresh cartridge of similar design. Openings 120 in cartridge retainer 106 allow visibility of the cartridge contents.

Medication cartridge 108 is of conventional design, including a body 122 having an interior reservoir filled with medication which is sealed at one end by a slidable plunger or piston 124 and sealed at the other end by a septum 126 held by a crimp ring 128.

A needle assembly 130 is detachably mountable to an externally threaded distal end 132 of cartridge retainer 106 and pierces the septum 126 when so mounted. The pierced septum through which the needle extends serves as an outlet during dispensing for the medication within the reservoir of body 122, which medication is delivered through the needle assembly 130 by operation of device 100. The cartridge 108 can hold multiple doses of medication, or even a single dose, depending on the purpose of device 100.

Medication delivery device 100 is shown in FIG. 7 in its "zero position" at which the device has not been set for delivery of any dose. In FIG. 8, device 100 is arranged after being manipulated to set a dose for delivery.

Medication delivery device 100 is typical of many such devices in including a manually-powered dose delivery mechanism that controls forward advancement of a drive member, generally designated at 134. Drive member 134 advances within the cartridge body 122 to directly engage and advance plunger 124. The dose delivery mechanism includes a dose knob 136 connected via dial sleeve 62 to a mechanical drive assembly within housing 42. When dose knob 136 is turned by a user to set a dose for delivery, dose knob 136 and dial sleeve 62 screw out together from housing 42. When a user applies a plunging force on the proximal end 140 of dose knob 136, the resulting forward motion of dose knob 136 and dial sleeve 62 into housing 42 is converted by the mechanical drive assembly into a smaller motion of drive member 134 forward from housing 42 into the interior of cartridge body 122.

Drive member 134 is formed in two pieces including a forward end 142 that directly engages the cartridge plunger 124, and a shaft 144 that axially extends from housing 42. The shaft 144 has external threads 146 and is engaged with the mechanical drive assembly to be driven out from housing 42. Forward end 142 is provided in the form of an enlarged foot that is mounted on shaft 144.

A controller 148 (FIG. 8) is operably connected to the sensing system to receive the outputs from the sensor. The controller may include conventional components such as a processor, power supply, memory, microcontrollers, etc. Controller 148 is shown in FIG. 8 as being located on the medication delivery device. Alternatively, all or part of the controller may be provided separately, such as by means of a computer, smart phone or other device. Means are then provided to operably connect the controller components with the sensor at appropriate times, such as by a wired or wireless connection.

The controller is configured to receive at least one output from the sensor during each of dose setting and dose delivery, from which may be determined the amount of dose set and the amount of dose delivered by operation of the medication delivery device. In one approach, the sensor provides outputs corresponding to the start and end relative rotational positions during dose setting and during dose delivery. The start and end positions are used to determine the amount of the dose set and delivered, such as by comparison to a stored table. In another aspect, the sensor may detect the relative rotational movements from start to finish of the dose setting and/or delivering phases by "counting" the passage of identifiable landmarks such as peaks in a cyclic response, which further may correspond to whole or half units of dose. General methods of converting specific sensor outputs into dose determinations are well known in the art and are contemplated by the present invention. The claimed sensing systems are not limited to any particular method in this regard.

The determined amounts of the dose set and of the dose delivered may be recorded by the medication delivery device and displayed to the patient. An alarm may be provided in the event the dose setting falls outside of an acceptable range. Similarly, an alarm may be provided if the amount of dose delivered does not correspond to the amount set, which may for example be an indication that not all of the set dose was delivered or that the device has otherwise malfunctioned.

Since the sensing system measures relative movement, the particular members with which the sensor and target are associated are completely reversible. However, the placement of the two sensor components may be dictated to some extent on other factors, such as the space that is available. Positioning of the sensor on the housing is advantageous to facilitate its connection to a power supply and with electronics used to receive, process, display and record the determined amounts of dose that are set and delivered. In a typical embodiment, the sensor is secured with an outer member such as the housing, and the target is secured with an opposed, inner member. However, it will be appreciated by those skilled in the relevant art that for any embodiment of the present invention the placement of the sensor and the target may be reversed.

While the invention has been illustrated and described in detail in the drawings and foregoing description, the same is to be considered as illustrative and not restrictive in character. All changes, equivalents, and modifications that come within the spirit of the inventions defined by the claims included herein are desired to be protected.

What is claimed is:

1. A sensing system for determining both the amount of a dose set and the amount of a dose delivered by operation of a medication delivery device, the sensing system comprising:
   a first member of the medication delivery device;
   a second member of the medication delivery device, the second member being rotatable relative to the first member;
   a third member of the medication delivery device rotatable relative to the first member during dose setting in proportion to the amount of a dose set by operation of the medication delivery device;
   a fourth member of the medication delivery device rotatable relative to the first member during dose delivery in proportion to the amount of a dose delivered by operation of the medication delivery device;
   the second member being rotationally coupled with the third member and not the fourth member during dose setting to rotate with the third member during dose setting, the second member being rotationally coupled with the fourth member and not the third member during dose delivery to rotate with the fourth member during dose delivery;
   a rotational sensor system comprising a first sensor component secured with the first member, and a second sensor component secured with the second member, one of the first and second sensor components being a target and the other of the first and second sensor components being a sensor configured to detect rotation of the target relative to the sensor,
   the rotational sensor system being operable during dose setting to detect the rotation of the target relative to the sensor and to generate at least one first output correlated thereto, and the rotational sensor system being operable during dose delivery to detect the rotation of the target relative to the sensor and to generate at least one second output correlated thereto.

2. The sensing system of claim 1 in which the first member is a housing of the medication delivery device and the second member is fixed axially relative to the housing.

3. The sensing system of claim 2 in which one of the housing and the second member includes a radially-extending flange, and the other of the housing and the second member includes a complementary groove receiving the flange and fixing the second member axially to the housing.

4. The sensing system of claim 1 in which the third and fourth members move axially in unison between a setting position and a delivery position relative to the second member.

5. The sensing system of claim 1 and further comprising a controller operably connected to the sensor to receive the at least one first output and the at least one second output from the sensor, the controller being configured to determine from the received at least one first output the amount of dose set by operation of the medication delivery device, and the controller being configured to determine from the received at least one second output the amount of dose delivered by operation of the medication delivery device.

6. The sensing system of claim 5 in which the controller is configured to receive two separate first outputs from the sensor corresponding to the start and end relative positions of the first and second members during dose setting and to determine therefrom the amount of the dose set, and the controller being further configured to receive two separate second outputs from the sensor corresponding to the start and end relative positions of the first and second members during dose delivery and to determine therefrom the amount of the dose delivered.

7. The sensing system of claim 1 in which the fourth member is fixed against movement relative to the first member during dose setting, and in which the third member is fixed against movement relative to the first member during dose delivery.

8. The sensing system of claim 1 and further comprising a first coupling system coupling the second member with the third member during dose setting, and a second coupling system coupling the second member with the fourth member during dose delivery.

9. The sensing system of claim 8 in which the first coupling system is configured to couple the second member with the third member upon axial movement of the third member relative to the second member in a first direction, and in which the second coupling system is configured to couple the second member with the fourth member upon axial movement of the fourth member relative to the second member in a second direction opposite the first direction.

10. The sensing system of claim 9 in which the third and fourth members move axially in unison between a setting position and a delivery position relative to the second member.

11. The sensing system of claim 10 in which the second member is positioned axially between the third and fourth members.

12. The sensing system of claim 11 in which the first coupling system comprises mutually-facing splines on the second and third members which engage or disengage upon axial movement of the third member relative to the second member, and in which the second coupling system comprises mutually-facing splines on the second and fourth members which engage or disengage upon axial movement of the fourth member relative to the second member.

13. A medication delivery device for determining both the amount of a dose set and the amount of a dose delivered by operation of the medication delivery device, comprising:
a first member;
a second member rotatable relative to the first member;
a third member rotatable relative to the first member during dose setting in proportion to the amount of a dose set by operation of the medication delivery device;
a fourth member rotatable relative to the first member during dose delivery in proportion to the amount of a dose delivered by operation of the medication delivery device;
the second member being rotationally coupled with the third member and not the fourth member during dose setting to rotate with the third member during dose setting, the second member being rotationally coupled with the fourth member and not the third member during dose delivery to rotate with the fourth member during dose delivery;
a rotational sensor system comprising a first sensor component secured with the first member, and a second sensor component secured with the second member, one of the first and second sensor components being a target and the other of the sensor components being a sensor configured to detect rotation of the target relative to the sensor,
the rotational sensor system being operable during dose setting to detect the rotation of the target relative to the sensor and to generate at least one first output correlated thereto, and the rotational sensor system being operable during dose delivery to detect the rotation of the target relative to the sensor and to generate at least one second output correlated thereto.

14. The medication delivery device of claim 13 which includes a housing and in which the first member is the housing and the second member is fixed axially relative to the housing.

15. The medication delivery device of claim 14 in which one of the housing and the second member includes a radially-extending flange, and the other of the housing and the second member includes a complementary groove receiving the flange and fixing the second member axially to the housing.

16. The medication delivery device of claim 13 in which the third and fourth members move axially in unison between a setting position and a delivery position relative to the second member.

17. The medication delivery device of claim 13 and further comprising a controller operably connected to the sensor to receive the at least one first output and the at least one second output from the sensor, the controller being configured to determine from the received at least one first output the amount of dose set by operation of the medication delivery device, and the controller being configured to determine from the received at least one second output the amount of dose delivered by operation of the medication delivery device.

18. The medication delivery device of claim 17 in which the controller is configured to receive two separate first outputs from the sensor corresponding to the start and end relative positions of the first and second members during dose setting and to determine therefrom the amount of the dose set, and the controller being further configured to receive two separate second outputs from the sensor corresponding to the start and end relative positions of the first and second members during dose delivery and to determine therefrom the amount of the dose delivered.

19. The medication delivery device of claim 13 in which the fourth member is fixed against movement relative to the first member during dose setting, and in which the third member is fixed against movement relative to the first member during dose delivery.

20. The medication delivery device of claim 13 and further comprising a first coupling system coupling the second member with the third member during dose setting, and a second coupling system coupling the second member with the fourth member during dose delivery.

21. The medication delivery device of claim 20 in which the first coupling system is configured to couple the second member with the third member upon axial movement of the third member relative to the second member in a first direction, and in which the second coupling system is configured to couple the second member with the fourth member upon axial movement of the fourth member relative to the second member in a second direction opposite the first direction.

22. The medication delivery device of claim 21 in which the third and fourth members move axially in unison between a setting position and a delivery position relative to the second member.

23. The medication delivery device of claim 22 in which the second member is positioned axially between the third and fourth members.

24. The medication delivery device of claim 23 in which the first coupling system comprises mutually-facing splines on the second and third members which engage or disengage upon axial movement of the third member relative to the second member, and in which the second coupling system comprises mutually-facing splines on the second and fourth members which engage or disengage upon axial movement of the fourth member relative to the second member.

* * * * *